United States Patent [19]

Demark

[11] Patent Number: 5,328,466
[45] Date of Patent: Jul. 12, 1994

[54] SYRINGE AND NEEDLE ASSEMBLY

[76] Inventor: Kristine E. Demark, 700 Gawain Rd., Plymouth Meeting, Pa. 19462

[21] Appl. No.: 92,503

[22] Filed: Jul. 15, 1993

[51] Int. Cl.⁵ .................. A61M 11/00; A61M 5/00; A61M 5/32
[52] U.S. Cl. .................................... 604/93; 604/189; 604/240
[58] Field of Search .............. 604/111, 240–243, 604/187, 189, 192

[56] References Cited

U.S. PATENT DOCUMENTS

| | | | |
|---|---|---|---|
| 3,391,694 | 7/1968 | Spaeth | 604/189 |
| 3,450,135 | 6/1969 | Sarnoff | 604/240 |
| 4,573,978 | 3/1986 | Reilly | 604/240 |
| 4,923,447 | 5/1990 | Morgan | 604/198 |
| 5,061,251 | 10/1991 | Juhasz | 604/198 |
| 5,205,833 | 4/1993 | Harsh et al. | 604/240 |
| 5,242,405 | 9/1993 | Howe | 604/125 |

FOREIGN PATENT DOCUMENTS 0440047  8/1991  European Pat. Off. ........... 604/111

*Primary Examiner*—John D. Yasko
*Assistant Examiner*—Adam J. Cermak
*Attorney, Agent, or Firm*—Charles Bergere

[57] ABSTRACT

A syringe and needle assembly having a means to align the beveled tip of the needle with the volumetric scale on the syringe is disclosed. In the preferred embodiment, a visible mark is placed longitudinally on the hub of the needle on the same side and in coaxial alignment with the beveled tip of the needle. This allows for the needle to be installed on the syringe and the beveled tip quickly aligned with the volumetric scale printed on the syringe body without the need for removing the needle safety cap prior to or during installation.

9 Claims, 1 Drawing Sheet

SYRINGE AND NEEDLE ASSEMBLY

FIELD OF THE INVENTION

This invention relates to syringes utilized for introducing or withdrawing fluids into the body of a human or an animal, and more particularly to a syringe and needle assembly providing a means for quickly and safely aligning the beveled tip of the needle with the volumetric scale imprinted on the syringe body.

BACKGROUND OF THE INVENTION

Common medical syringes are well known and have been used for many years both to inject fluids into a body and to withdraw fluids from a body. A typical syringe comprises a cylindrical syringe body having a needle receiving end and a plunger slidably disposed within the body to control the discharge or withdrawal of fluid therefrom. In order to accurately monitor the withdrawal and discharge of fluid from the syringe body, a volumetric scale is imprinted on one side of the syringe body. The needle receiving end is adapted to mate with a hypodermic needle assembly, the needle assembly typically comprising a hub adapted to engage the syringe needle receiving end, and a hypodermic needle having a beveled tip.

The syringe comes in a sterile holder and the needle assembly is provided for separately, and comes with a color-coded cap over the needle and a clear cap over the hub. These caps keep the needle sterile, with the color-coded needle cup further providing a means to determine the gauge size of the needle (e.g. pink=20 gauge, blue=22 gauge, and white=16 gauge). Thus, the assembly procedure is to remove the syringe from its holder, choose the proper gauge needle, and pull the clear cap off of the hub, and then connect the hub to the syringe. It is preferred that the colored-cap remain on the needle during assembly in order to prevent harmful contact and to insure the needle remains sterile.

When inserting the needle into a vein, it is inserted with the bevel side up. Often times when anesthetizing an animal or a patient, the syringe has more drug than necessary, so you only want to give to effect, that is, until the animal is sleeping. This dosage varies depending on, among other things, the size of the animal and the strength of the drug. Thus, you must carefully monitor how much drug is administered, since overdose is dangerous. Generally, the drug is given in 0.1 cc increments. In order to monitor this rate, it is preferred that the volumetric scale imprinted on the syringe is facing up. Similarly, when taking blood from a patient, only a certain amount is required, e.g. for blood tests about 1.0 cc, so again, it is preferred to have the volumetric scale facing up.

Normally, the needle is inserted into the body of the animal/patient with the bevel side up. However, in order to allow the volumetric scale on the syringe body to face up, it must be aligned with the bevel on the needle. Presently, this task is both difficult and time consuming because the bevel on the needle cannot be seen through the colored cap. In order to prealign the bevel of the needle with the imprinted scale on the syringe body, the colored cap may have to be removed and replaced repeatedly during adjustment, exposing it to a less sterile environment and increasing the likelihood of potentially hazardous contact with the doctor, nurse, or caregiver. Moreover, in emergency situations, the syringe and needle assembly must be connected as quickly as possible. Thus, there is a need to be able to align the beveled tip of the needle with the imprinted scale on the syringe body.

Heretofore, no method or means has been provided to quickly and easily align the beveled tip of the needle with the volumetric scale on the syringe body, Thus, the tedious and potentially dangerous process of repeatedly removing the color coded cap to check alignment, replacing the cap and adjusting the needle is required.

SUMMARY OF THE INVENTION

It is an object of the present invention to provide a means to align the beveled tip of a hypodermic needle with the imprinted volumetric scale on the body of a syringe, without the need of removing the safety cap on the needle.

Briefly stated, the present invention is a syringe and needle assembly wherein the hub of the needle has a clearly visible mark on it which indicates the position of the bevel on the needle. The present invention provides for a quicker, safer, and more efficient method of assembling a syringe and needle prior to usage.

BRIEF DESCRIPTION OF THE DRAWINGS

The foregoing summary, as well as the following detailed description of the presently preferred embodiments of the invention will be better understood when read in conjunction with the appended drawings. For the purpose of illustrating the invention, there is shown in the drawings, an embodiment which is presently preferred. It should be understood, however, that the present invention is not limited to the particular arrangement and instrumentality shown. In the drawings.

DETAILED DESCRIPTION OF THE INVENTION

Figure 1:
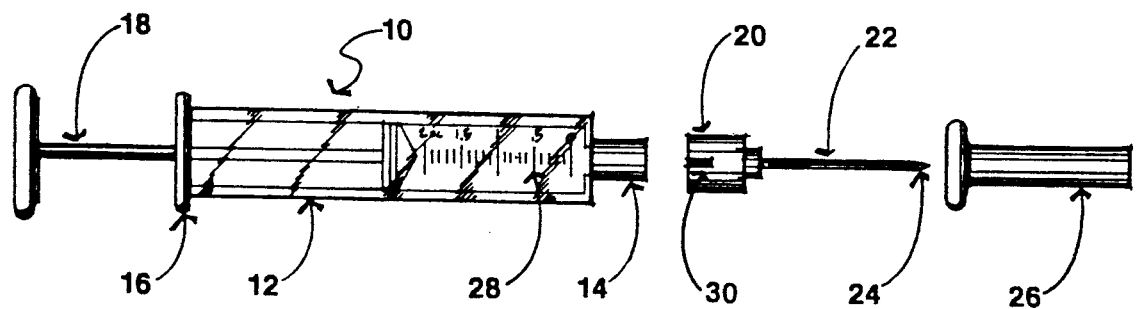
FIG. 1 is a side elevational view of a syringe and needle assembly of the present invention.

Certain terminology is used in the following description for convenience only and is not limiting. The words "right," "left," "lower," and "upper" designate directions in the drawings to which reference is made. The words "forwardly" and "rearwardly" refer to directions toward and away from, respectively, the geometric center of the syringe body and designated parts thereof. The term "coaxial alignment" denotes two or more objects facing in the same lateral direction. The terminology includes the words above specifically mentioned, derivatives thereof and words of similar import.

Figure 3:
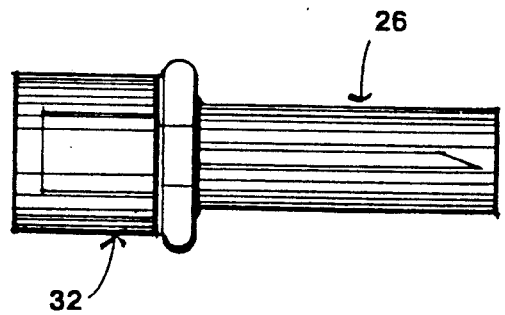
FIG. 3 is a side view of a needle assembly with its caps installed thereon.
Figure 2:
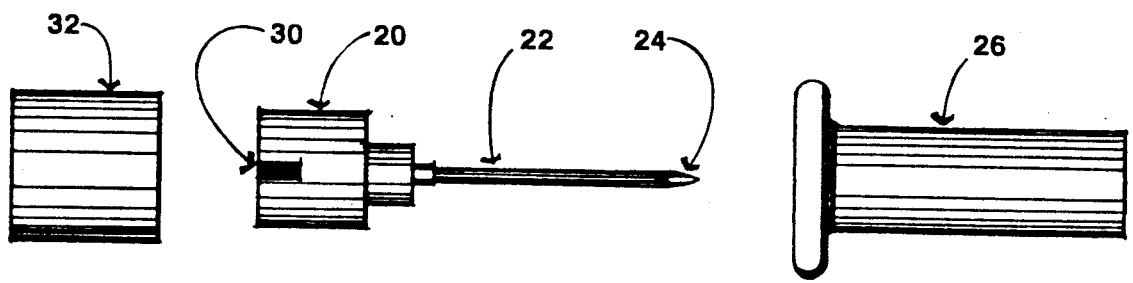
FIG. 2 is a side view of a typical needle assembly embodying the present invention.

Referring to the drawings in detail, wherein like numerals indicate like elements throughout, there is shown in FIGS. 1 through 3 a preferred embodiment of a syringe and needle assembly 10 in accordance with the present invention. Referring to FIG. 1, there is shown a syringe and needle assembly 10 which comprises a cylindrical syringe body 12 having a needle receiving end 14 and a plunger receiving end 16. A plunger 18 is slidably positioned within the cylindrical body 12 and is designed to permit fluid within the body 12 to be dispensed there from in a desired quantity and at a desired rate by moving the plunger forwardly into the body 12. Additionally, fluid may be drawn into the syringe body by moving the plunger 18 rearwardly. The needle receiving end 14 is adapted to engage a needle hub 20. A variety of methods are commonly employed to securely engage the hub 20 to syringe receiving end 14 such as a threaded end and screw on hub or just a push on hub.

The hub 20 is in fluid engagement with hypodermic needle 22 having a beveled tip 24 and a safety cap 26. The needle is provided in various sizes, measured by the gauge of the needle 22. In order to determine the needle size, safety cap 26 is color coded to the gauge size of needle 22.

The syringe body 12 is imprinted with a fluid volumetric scale 28 to facilitate administering the proper dosage or to insure an adequate amount of fluid is withdrawn from the patient for the required purpose. Visible mark 30 is provided on needle hub 20 as a means to align the beveled tip 24 with volumetric scale 28. Visible mark 30 is placed on hub 20 in coaxial alignment with beveled tip 24. It is envisioned that visible mark 30 comprises a mark, slot, groove, or other clearly visible means for aligning the beveled tip 24 with the volumetric scale 28 without the need for removing safety cap 26. Further, the mark 30 may be colored in order to enhance its visibility.

FIG. 2 shows needle 22 with beveled tip 24, hub 22 and alignment means 30. Also shown are safety cap 26 and hub cap 32. These caps 26, 32 maintain the needle in a sterile environment prior to use, and as previously discussed, cap 26 also may be color coded to the gauge size needle 22.

FIG. 3 shows the needle 22 with caps 26 and 32 installed thereon. When cap 26 is covering needle 22, it cannot be determined which side of the needle tip 24 is beveled. Thus requiring cap 26 be removed after installation on syringe end 14 to determine if needle tip 24 is aligned with scale 28. However, when needle hub 20 is provided with alignment means 30, needle 22 with cap 26 may be quickly and safely installed and aligned on syringe needle receiving end 14.

Although particular embodiments of the present invention have been described, it will be apparent to those skilled in the art that various changes and modifications can be made without departing form the spirit and scope of the present invention. It is intended that the appended claims encompass such changes and modifications as fall within the scope of the present invention.

What is claimed is:

1. A syringe assembly comprising:
   an elongated tubular syringe body for holding a volume of fluid having a plunger end and a needle receiving end, said syringe body including a means for measuring the volume of fluid therein;
   a plunger slidably engaged within said syringe body for aspirating or injecting fluid from said syringe body;
   a hypodermic needle having a hub end and a beveled tip, said beveled tip facing in at least one lateral direction; wherein said hub end is adapted to mate with said syringe body needle receiving end; and
   a means on said hypodermic needle facing said at least one lateral direction for aligning said beveled tip with said fluid volume measuring means.

2. The device of claim 1 wherein said alignment means comprises a longitudinal notch in said hub end, said notch being disposed on said hub in coaxial relation to said beveled tip.

3. The device of claim 2 wherein said notch is colored so that it is readily visible.

4. The device of claim 1 wherein said alignment means comprises a longitudinal line in said hub end, said line positioned on said hub in coaxial relation to said beveled tip.

5. A hypodermic needle assembly for attaching to a syringe, said syringe having a volumetric scale imprinted on its side, comprising:
   a needle with a beveled tip end, said beveled tip facing in at least one lateral direction;
   a needle hub end opposite said beveled tip end, said hub end adapted to engage with said syringe; and
   a means on said needle assembly facing said at least one lateral direction for aligning said beveled tip with said volumetric scale.

6. The apparatus according to claim 5 wherein said alignment means comprises a visible notch on said hub, said notch placed in relation to said beveled tip so that when the needle assembly is attached to said syringe, the beveled tip can be aligned with said volumetric scale by twisting the needle until the notch is in coaxial alignment with said scale.

7. The apparatus according to claim 5 wherein said alignment means comprises a groove on said hub, said groove placed in relation to said beveled tip so that when the needle assembly is attached to said syringe, the beveled tip can be aligned with said volumetric scale by twisting the needle until the groove is in coaxial alignment with said scale.

8. The apparatus according to claim 5 wherein said means to align comprises a mark on said hub, said imprint placed in relation to said beveled tip so that when the needle assembly is attached to said syringe, the beveled tip can be aligned with said volumetric scale by twisting the needle until the imprint is in coaxial alignment with said scale.

9. A method of aligning a beveled tip on a hypodermic needle with a volumetric scale on a syringe body comprising the steps of:
   removing a syringe from a sterile package;
   choosing a needle to attach to said syringe, said needle having a beveled tip end and a hub end, the hub end having a visible marking longitudinally disposed thereon in coaxial alignment with the beveled tip, both of said ends covered with safety caps;
   removing the hub end safety cap from the needle;
   attaching the needle hub end to the syringe body;
   twisting the needle until said marking on the hub is aligned with the volumetric scale on said syringe; and
   removing the needle tip safety cap.

* * * * *